United States Patent
Elliott et al.

(10) Patent No.: US 6,620,826 B2
(45) Date of Patent: Sep. 16, 2003

(54) ENDOTHELIN RECEPTOR ANTAGONISTS

(75) Inventors: John Duncan Elliott, Wayne, PA (US); Joseph Weinstock, Phoenixville, PA (US); Jia-Ning Xiang, Wayne, PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 10/353,499

(22) Filed: Jan. 29, 2003

(65) Prior Publication Data

US 2003/0153567 A1 Aug. 14, 2003

Related U.S. Application Data

(63) Continuation of application No. 10/135,541, filed on Apr. 30, 2002, now abandoned, which is a continuation of application No. 08/522,285, filed as application No. PCT/US95/10885 on Aug. 28, 1995, now abandoned, which is a continuation of application No. 08/476,992, filed on Jun. 7, 1995, now abandoned, and a continuation of application No. 08/375,318, filed on Jan. 18, 1995, now abandoned, and a continuation of application No. 08/300,829, filed on Sep. 2, 1994, now abandoned.

(51) Int. Cl.$^7$ ............ C07D 317/48; C07D 405/06; A61K 31/4178

(52) U.S. Cl. ............ 514/341; 514/235.8; 514/254.05; 514/256; 514/326; 514/400; 514/382; 514/397; 544/370; 544/333; 544/139; 546/210; 546/275.1; 548/252; 548/311.7; 548/338.5; 548/340.1; 548/312.1; 548/315.1; 548/314.4; 548/312.4

(58) Field of Search ............ 514/382, 397, 514/341, 400, 326, 254.05, 256, 235.8; 548/252, 311.7, 338.5, 340.1, 312.1, 315.1, 314.4, 312.4; 546/275.1, 210; 544/370, 333, 139

(56) References Cited

U.S. PATENT DOCUMENTS

| 4,006,137 A | 2/1977 | Haugwitz et al. ............ 260/240 |
| 4,760,150 A | 7/1988 | Sato et al. ............ 548/336 |

FOREIGN PATENT DOCUMENTS

| EP | 0 403 158 | 12/1990 |
| EP | 0 403 159 | 12/1990 |
| WO | WO 92/10189 | 6/1992 |
| WO | WO 94/02474 | 3/1994 |

OTHER PUBLICATIONS

Douglas, Clinical Development of Endothelin Receptor Antagonists, TiPS, vol. 18, ppg. 408–412, Nov. 1997.

Pollock et al., Pub Med Abstract (Ren. Fall., 19(6): 753–61), Nov. 1997.

Shimizu et al. Pub Med. Abstract (J. Pharm. Exp. Ther., 286(2): 977–983), Aug. 1998.

Ronco, PubMed Abstract (Bull. Acad. Natl. Med., 183(1): 65–77), 1999.

Venkataraman, PubMed Abstract (Expert Opin. Investig. Drugs, (11): 2579–92) Nov., 2000.

*Primary Examiner*—Deepak Rao
(74) *Attorney, Agent, or Firm*—Linda E. Hall; Stephen Venetianer; Charles M. Kinzig

(57) ABSTRACT

Novel N-phenyl imidazole derivatives, pharmaceutical compositions containing these compounds and their use as endothelin receptor antagonists are described.

9 Claims, No Drawings

ENDOTHELIN RECEPTOR ANTAGONISTS

This is a continuation of application Ser. No. 10/135,541 filed Apr. 30, 2002 now abandoned; which is a continuation of application Ser. No. 08/522,285 filed Apr. 28, 1997 now abandoned; which is a 371 of International Application No. PCT/US95/10885, filed Aug. 28, 1995; which is a continuation claims priority to application Ser. Nos. 08/300,829, filed Sep. 2, 1994 now abandoned; 08/375,318, filed Jan. 18, 1995 now abandoned; and 08/476,992, filed Jun. 7, 1995 now abandoned.

FIELD OF INVENTION

The present invention relates to novel N-phenyl imidazole derivatives, pharmaceutical compositions containing these compounds and their use as endothelin receptor antagonists.

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity, radio contrast induced renal failure and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al. Br. J. Pharm. 99: 597–601, 1989 and Clozel and Clozel, Circ. Res., 65: 1193–1200, 1989) coronary vasospasm (Fukuda et al., Eur. J. Pharm. 165: 301–304, 1989 and Lüscher, Circ. 83: 701, 1991) heart failure, proliferation of vascular smooth muscle cells, (Takagi, Biochem & Biophys. Res. Commun.; 168: 537–543, 1990, Bobek et al., Am. J. Physiol. 258:408-C415, 1990) and atherosclerosis, (Nakaki et al., Biochem. & Biophys. Res. Commun. 158: 880–881, 1989, and Lerman et al., New Eng. J. of Med. 325: 997–1001, 1991). Increased levels of endothelin have been shown after coronary balloon angioplasty (Kadel et al., No. 2491 Circ. 82: 627, 1990).

Further, endothelin has been found to be a potent constrictor of isolated mammalian airway tissue including human bronchus (Uchida et al., Eur J. of Pharm. 154: 227–228 1988, LaGente, Clin. Exp. Allergy 20: 343–348, 1990; and Springall et al., Lancet, 337: 697–701, 1991). Endothelin may play a role in the pathogenesis of interstitial pulmonary fibrosis and associated pulmonary hypertension, Glard et al., Third International Conference on Endothelin, 1993, p. 34 and ARDS (Adult Respiratory Distress Syndrome), Sanai et al, Supra, p. 112.

Endothelin has been associated with the induction of hemorrhagic and necrotic damage in the gastric mucosa (Whittle et al., Br. J. Pharm. 95: 1011–1013, 1988); Raynaud's phenomenon, Cinniniello et al., Lancet 337: 114–115, 1991); Crohn's Disease and ulcerative colitis, Munch et al., Lancet, Vol. 339, p. 381; Migraine (Edmeads, Headache, February 1991 p 127); Sepsis (Weitzberg et al., Circ. Shock 33: 222–227, 1991; Pittet et al., Ann. Surg. 213: 262–264, 1991), Cyclosporin-induced renal failure or hypertension (Eur. J. Pharmacol., 180: 191–192, 1990, Kidney Int, 37: 1487–1491, 1990) and endotoxin shock and other endotoxin induced diseases (Biochem. Biophys. Res. Commun., 161: 1220–1227, 1989, Acta Physiol. Scand. 137: 317–318, 1989) and inflammatory skin diseases. (Clin Res. 41:451 and 484, 1993).

Endothelin has also been implicated in preclampsia of pregnancy. Clark et al., Am. J. Obstet. Gynecol. March 1992, p. 962–968; Kamor et al., N. Eng. J. of Med., Nov. 22, 1990, p. 1486–1487; Dekker et al., Eur J. Ob. and Gyn. and Rep. Bio. 40 (1991) 215–220; Schiffet al., Am. J. Ostet. Gynecol. February 1992, p. 624–628; diabetes mellitus, Takahashi et al., Diabetologia (1990) 33:306–310; and acute vascular rejection following kidney transplant, Watschinger et al., Transplantation Vol. 52, No. 4, pp. 743–746.

Endothelin stimulates both bone resorption and anabolism and may have a role in the coupling of bone remodeling. Tatrai et al. Endocrinology, Vol. 131, p. 603–607.

Endothelin has been reported to stimulate the transport of sperm in the uterine cavity, Casey et al., J. Clin. Endo and Metabolism, Vol. 74, No. 1, p. 223–225, therefore endothelin antagonists may be useful as male contraceptives. Endothelin modulates the ovarian/menstrual cycle, Kenegsberg, J. of Clin. Endo. and Met., Vol. 74, No. 1, p. 12, and may also play a role in the regulation of penile vascular tone in man, Lau et al., Asia Pacific J. of Pharm., 1991, 6:287–292 and Tejada et al., J. Amer. Physio. Soc. 1991, H1078–H1085. Endothelin also mediates a potent contraction of human prostatic smooth muscle, Langenstroer et al., J. Urology, Vol. 149, p. 495–499.

Thus, endothelin receptor antagonists would offer a unique approach toward the pharmacotherapy of hypertension, renal failure, ischemia induced renal failure, sepsis-endotoxin induced renal failure, prophylaxis and/or treatment of radio-contrast induced renal failure, acute and chronic cyclosporin induced renal failure, cerebrovascular disease, myocardial ischemia, angina, heart failure, asthma, pulmonary hypertension, pulmonary hypertension secondary to intrinsic pulmonary disease, atherosclerosis, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention of restenosis, diabetes, preclampsia of pregnancy, bone remodeling, kidney transplant, male contraceptives, infertility and priaprism and benign prostatic hypertrophy.

SUMMARY OF THE INVENTION

This invention comprises compounds represented by Formula (I) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, benign prostatic hypertrophy, pulmonary hypertension, migraine, stroke, cerebrovascular vasospasm, myocardial ischemia, angina, heart failure, atherosclerosis, and as an adjunct in angioplasty for prevention of restenosis.

This invention further constitutes a method for antagonizing endothelin receptors in an animal, including humans, which comprises administering to an animal in need thereof an effective amount of a compound of Formula (I).

DETAILED DESCRIPTION OF THE INVENTION

The compounds of this invention are represented by structural Formula (I):

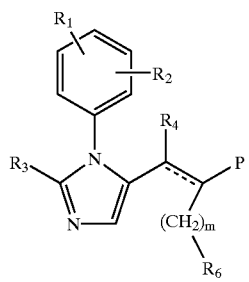

(I)

wherein:

$R_1$ is H, $C_{1-6}$alkyl or $C_{1-6}$alkoxy;

$R_2$ is $XR_5$, —$R_8CO_2R_4$, —$(CH_2)_xC(O)N(R_4)S(O)_yR_9$, —$(CH_2)_xS(O)_yN(R_4)C(O)R_9$, —$CH_2)_xC(O)N(R_4)C(O)R_9$, —$(CH_2)_nR_7$, —$(CH_2)_xS(O)_yN(R_4)S(O)_yR_9$ or Ar;

X is O, S or $NR_4$;

$R_3$ is $C_{1-10}$alkyl, $XC_{1-10}$alkyl, Ar or XAr;

$R_4$ is hydrogen or $C_{1-6}$alkyl;

$R_5$ is —$R_8CO_2R_4$, —$(CH_2)_xC(O)N(R_4)S(O)_yR_9$, —$(CH_2)_xS(O)_yN(R_4)C(O)R_9$, —$C(O)N(R_4)_2$, —$(CH_2)_xC(O)N(R_4)C(O)R_9$, —$(CH_2)_xS(O)_yN(R_4)S(O)_yR_9$, —$(CH_2)_nCO_2R_4$, —$(CH_2)_nR_7$ or Ar;

$R_6$ is $C_{1-8}$alkyl or —Ar,

P is tetrazol-5-yl, $CO_2R_4$ or $C(O)N(R_4)S(O)_yR_9$;

$R_7$ is $C_{1-6}$alkoxy, $C_{1-6}$alkyl, hydroxy, —$SC_{1-6}$alkyl, —$NHSO_2R_9$, $SO_2NHR_9$, —$SO_3H$, —$CO(NR_4)_2$, CN, —$S(O)_yC_{1-6}$alkyl, —$PO(OR_4)_2$, —$N(R_4)_2$, —$NR_4CHO$, —$NR_4COC_{1-6}$alkyl, —$NR_4CON(R_4)_2$ or Ar, or $R_7$ is tetrazolyl, which is substituted or unsubstituted by $C_{1-6}$alkyl, $CF_3$ or $C(O)R_3$;

$R_8$ is $C_{1-4}$alkylene, $C_{1-4}$alkenylene or $C_{1-4}$alkylidene, all of which may be linear or branched;

$R_9$ is $C_{1-10}$alkyl, $N(C_{1-8}$alkyl$)_2$ or Ar;

n is 1 to 4;

m is 0 to 3;

x is 0 to 4;

y is 1 or 2;

Ar is:

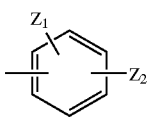

(a)

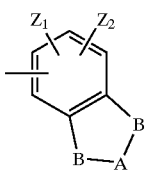

(b)

naphthyl, indolyl, pyridyl, thienyl, oxazolidinyl, thiazolyl, isothiazolyl, pyrazolyl, imidazolyl, imidazolinyl, thiazolidinyl, isoxazolyl, oxadiazolyl, thiadiazolyl, morpholinyl, piperidinyl, piperazinyl, pyrrolyl, or pyriridyl; all of which may be substituted or unsubstituted by one or more $Z_1$ or $Z_2$ groups;

$Z_1$ and $Z_2$ are independently hydrogen, $XR_4$, $C_{1-8}$alkyl, $CO_2R_4$, $C(O)N(R_4)_2$, CN, $NO_2$, F, Cl, Br, I, $N(R_4)_2$, $NHC(O)R_4$ or tetrazolyl which may be substituted or unsubstituted by $C_{1-6}$alkyl, $CF_3$ or $C(O)R_4$;

A is C=O or $[C(R_4)_2]_q$;

B is —$CH_2$— or —O—; and q is 1 or 2;

and the dotted line indicates the optional presence of a double bond;

or a pharmaceutically acceptable salt thereof;

provided:

$R_6$ is not thienyl; and $R_2$ is not $(CH)_nC_{1-6}$alkyl, or —CH=CHCO$_2R_4$.

All alkyl, alkenyl, alkynyl and alkoxy groups may be straight or branched.

The compounds of the present invention may contain one or more asymmetric carbon atoms and may exist in racemic and optically active form. All of these compounds and diastereoisomers are contemplated to be within the scope of the present invention.

Preferred compounds are those wherein there is an optional double bond present; $R_4$ is cis to P; $R_1$ is H or $C_{1-6}$alkoxy; $R_2$ is —$OR_5$, —$R_8CO_2H$, —$(CH_2)_xC(O)N(R_4)S(O)_yR_9$, —$(CH_2)_xC(O)NHC(O)R_9$, —$(CH_2)_nR_7$, or $R_2$ is phenyl or pyridyl, both of which may be substituted or unsubstituted by one or more $Z_1$ or $Z_2$ groups; $R_3$ is $C_{1-10}$alkyl, $C_{1-10}$alkoxy or $R_3$ is phenyl or pyrazolyl, both of which may be substituted or unsubstituted by $C_{1-6}$ alkoxy, Cl, Br, F or I; $R_4$ is hydrogen or $C_{1-6}$alkyl; $R_5$ is —$R_8CO_2H$, —$(CH_2)_xC(O)N(R_4)S(O)_yR_9$, —$(CH_2)_xC(O)NHC(O)R_9$, —$(CH_2)_nCO_2R_4$, —$(CH_2)_nR_7$ or pyridyl which may be substituted or unsubstituted by $Z_1$; $R_6$ is (a), (b) or indolyl; P is $CO_2H$ or $C(O)NHS(O)_yR_9$; $R_7$ is $C_{1-6}$alkoxy, $C_{1-6}$alkyl, piperidinyl, hydroxy, —$NHSO_2R_9$, —$CONHR_4$, —$N(R_4)_2$, —$NR_4CON(R_4)_2$ or $R_7$ is thienyl, pyridyl, pyrimidyl, phenyl, all of which may be substituted or unsubstituted by one or more $Z_1$ or $Z_2$ groups or $R_7$ is tetrazol-5-yl, piperazinyl both of which are substituted or unsubstituted by $C_{1-6}$alkyl; $R_8$ is $C_{1-4}$alkenylene which may be linear or branched; $R_9$ is $C_{1-10}$alkyl, $N(C_{1-8}alkyl)_2$ or phenyl which may be substituted or unsubstituted by $C_{1-8}$alkyl; n is 1 to 4; m is 1; x is 0 to 4; y is 1 or 2; $Z_1$ and $Z_2$ are independently hydrogen, hydroxy, $C_{1-8}$alkyl, $C_{1-6}$alkoxy, $CO_2H$, $C(O)N(R_4)_2$, F, Cl, Br, I, $N(R_4)_2$, or tetrazolyl which may be substituted or unsubstituted by $C_{1-6}$alkyl; A is $[C(R_4)_2]_q$; q is 1; and B is —O—.

More preferred are compounds wherein there is an optional double bond present; $R_4$ is cis to P; $R_1$ is H or $C_{1-3}$alkoxy; $R_2$ is —$(CH_2)_xC(O)NHS(O)_2R_9$, —$OR_5$, —$(CH_2)_nR_7$, or —$O(CH_2)_{1-3}CO_2H$; $R_3$ is $C_{1-5}$alkyl; $R_4$ is hydrogen; $R_5$ is —$(CH_2)_xC(O)NHS(O)_2R_9$, —$(CH_2)_xC(O)NHC(O)R_9$, —$(CH_2)_nR_7$ or pyridyl which may be substituted or unsubstituted by $Z_1$; $R_6$ is (b); P is $CO_2H$; $R_7$ is hydroxy, —$NHSO_2R_9$, —$CONH(C_{1-5}alkyl)$, or $R_7$ is tetrazol-5-yl or piperazinyl, both of which may be substituted or unsubstituted by $C_{1-6}$alkyl or $R_7$ is thienyl, pyridyl, pyrimidyl, or phenyl, all of which may be substituted or unsubstituted by one or more $Z_1$ or $Z_2$ groups; $R_9$ is $C_{1-5}$alkyl, $N(C_{1-5}alyl)_2$ or $R_9$ is phenyl which may be substituted or unsubstituted by $C_{1-5}$alkyl; n is 1 to 4; m is 1; x is 0 to 4; $Z_1$ and $Z_2$ are independently hydrogen, hydroxy, $C_{1-6}$alkoxy, $CO_2H$, $C(O)NH_2$, F, Cl, or tetrazolyl which may be substituted or unsubstituted by $C_{1-6}$alkyl; A is —$CH_2$—; and B is —O—.

Especially preferred are the following compounds:

(E)-3-[2-Butyl-1-[2-[N-(phenylsulfonyl)]carboxamidomethoxy-4-methoxyphenyl]-1H-imidazol-5-yl]-2-[(2-methoxy-4,5-methylenedioxy)phenylmethyl]-2-propenoic acid dipotassium;

(E)-3-[2-Butyl-1-[2-(tetrazol-5-yl)methoxy-4-methoxy]phenyl-1H-imidazol-5-yl]-2-[(2-methoxy-4,5-methylenedioxyphenyl)methyl]-2-propenoic acid;

(E)-3-[2-Butyl-1-[2-(2-carboxyphenyl)methoxy-4-methoxy]phenyl-1H-imdazol-5-yl]-2-[(2-methoxy-4,5-metlhylenedioxyphenyl)methyl]-2-propenoic acid;

(E)-3-[2-Butyl-1-[2-(4-carboxyphenyl)methoxy-4-methoxy]phenyl-1H-imidazol-5-yl]-2-[(2-methoxy-4,5-methylenedioxyphenyl)methyl]-2-propenoic acid;

E-3-[2-Butyl-1-[2-(3-carboxyphenyl)methoxy-4-methoxy]phenyl-1H-imidazol-5-yl]-2-[(2-methoxy-4,5-methylenedioxyphenyl)methyl]-2-propenoic acid;

E-3-(2-Butyl-1-[2-[N-(2-methylphenyl)sulfonyl]carboxamidomethoxy-4-methoxy]phenyl-1H-imidazol-5-yl-2-[(2-methoxy-4,5-methyl-enedioxyphenyl)methyl]-2-propenoic acid;

E-3-[2-Butyl-1-[2-[N-(4-methylphenyl)sulfonyl]carboxamidomethoxy-4-methoxy]phenyl-1H-imidazol-5-yl]-2-[(2-methoxy-4,5-methyl-enedioxyphenyl)methyl]-2-propenoic acid;

E-3-[2-Butyl-1-[2-(N-dimethylaminosulfonyl)carboxamidomethoxy-4-methoxy]phenyl-1H-imidazol-5-yl]-2-[(2-methoxy-4,5-methyl-enedioxyphenyl)methyl]-2-propenoic acid;

E-3-[2-Butyl-1-[2-(N-methanesulfonyl)carboxamidomethoxy-4-methoxy]phenyl-1H-imidazol-5-yl]-2-[(2-methoxy-4,5-methyl-enedioxyphenyl)methyl]-2-propenoic acid;

E-3-[2-Butyl-1-[2-(N-t-butylsulfonyl)carboxamidomethoxy-4-methoxy]phenyl-1H-imidazol-5-yl]-2-[(2-methoxy-4,5-methyl-enedioxyphenyl)methyl]-2-propenoic acid;

E-3-[2-Butyl-1-[2-(N-i-propylsulfonyl)carboxamidomethoxy-4-methoxy]phenyl-1H-imidazol-5-yl]-2-[(2-methoxy-4,5-methyl-enedioxyphenyl)methyl]-2-propenoic acid;

E-3-[2-Butyl-1-[2-(2-(tetrazol-5-yl)benzyloxy-4-methoxy]phenyl-1H-imidazol-5-yl]-2-[(2-methoxy-4,5-methylenedioxyphenyl)methyl]-2-propenoic acid;

E-3-[2-Butyl-1-[2-(2-ethyl-3H-tetrazol-5-yl)benzyloxy-4-methoxy]phenyl-1H-imidazol-5-yl]-2-[(2-methoxy-4,5-methylenedioxyphenyl)methyl]-2-propenoic acid;

E-3-[2-Butyl-1-[2-[(4-carboxypyridin-3-yl)oxy]4-methoxy]phenyl-1H-imidazol-5yl]-2-[(3,4-methylenedioxyphenyl)methyl]-2-propenoic acid;

(E)-3-[2-Butyl-[1-(2-carboxymethoxy)-4-methoxy)phenyl]-1H-imidazol-5-yl]-2-[(2-methoxy-4,5-methylenedioxyphenyl)methyl]-2-propenoic acid;

E-3-[2-Butyl-1-[2-(3-carboxy)propoxy-4-methoxy]phenyl-1H-imidazol-5-yl]-2-[(2-methoxy-4,5-methylenedioxyphenyl)methyl]-2-propenoic acid;

The present invention provides compounds of Formula (I),

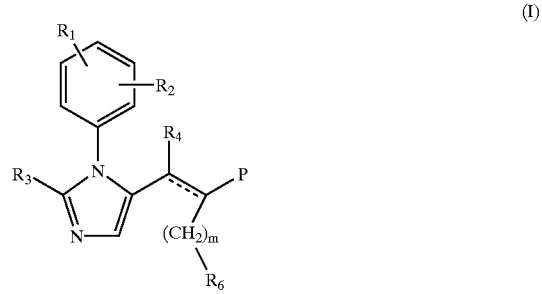

(I)

which can be prepared by reacting an aniline of Formula (2)

(2)

with an iminoether of Formula (3)

(3)

in a solvent such as dichloromethane at reflux to afford an amidine of Formula (4).

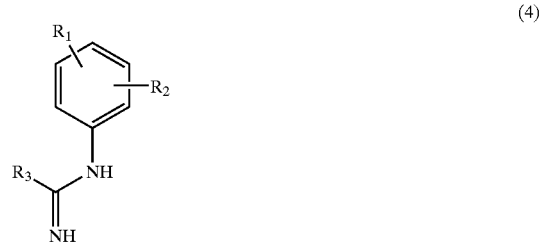

(4)

An iminoether of Formula (3) may be prepared from a nitrile of Formula (5)

(5)

by reaction with methanolic hydrogen chloride, in a solvent such as methyl alcohol, to provide the corresponding iminoether hydrochloride followed by liberation of (3) by treatment with a base such as triethylamine in a solvent such as diethyl ether. Filtration of the resulting product to remove triethylamine hydrochloride followed by evaporation of the solvent in vacuo provides (3).

Reaction of an amidine of Formula (4) with 2-bromomalondialdehyde (6)

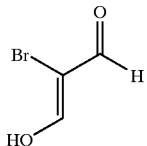
(6)

in a solvent such as isopropanol containing triethylammonium acetate at reflux affords an aldehyde of Formula (7).

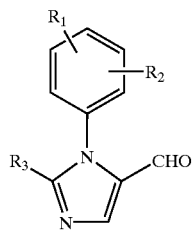
(7)

Knoevenagel condensation of a compound such as (7) with a half acid of Formula (8), wherein $R_6$ is Ar, m is 1 or 2, and $R_{10}$ is $C_{1-8}$alkyl,

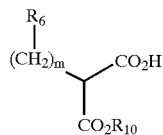
(8)

in a solvent such as benzene at reflux, in the presence of piperidinium acetate with azeotropic removal of water using a Dean-Stark apparatus, affords an ester of Formula (9).

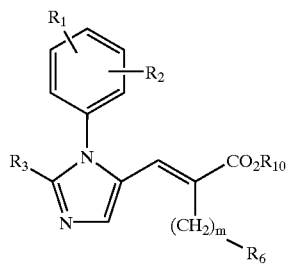
(9)

Saponification of an ester of Formula of (9) with aqueose sodium hydroxide in a solvent such as ethanol following acidic work up affords a compound of Formula of (1), where $R_4$ is H, and P is COOH.

Alternatively, hydrogenation of a compound of Formula (9) with hydrogen gas under pressure at approximately 60 psi in the presence of a suitable catalyst such as 10% palladium on charcoal in a suitable solvent such as ethyl acetate or ethanol affords a compound of Formula (10);

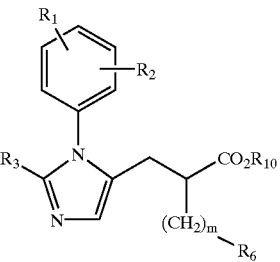
(10)

Saponification of an ester of Formula of (10) with aqeouse sodium hydroxide in a solvent such as ethanol following acidic work up affords a compound of Formula of (1), where there is an optional single bond, $R_4$ is H, P is COOH.

An aniline of Formula (11) may be prepared by reaction of a nitrophenol of Formula (13)

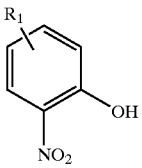
(13)

with bromomethyl methyl ether in a solvent such as dimethyl formamide in the presence of a base such as sodium hydride to afford an ether of Formula (14).

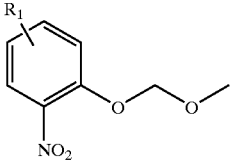
(14)

Reduction of an ether of Formula (14) using hydrogen in the presence of a catalyst such as 10% palladium on charcoal in a solvent such as ethanol affords a aniline of Formula (11).

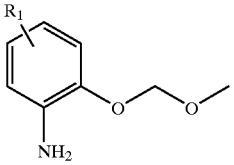
(11)

For compounds of Formula (I), wherein $R_2$ is $O(CH_2)_nR_7$ ($R_7$ is tetrazole or Ar) or $OCH_2CONHSO_2R_6$, $R_4$ is hydrogen, P is $CO_2H$, an aniline of Formula (11 is reacted as described above to provide an aldehyde of Formula (12).

(12)

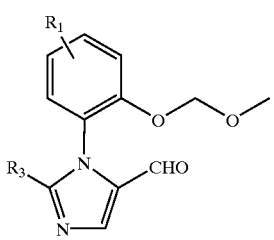

A malonic acid half ester of Formula (8), where $R_6$ is (b), A is —$CH_2$—, B is —O—, and m is 1, may be prepared from an aldehyde such as (15)

(15)

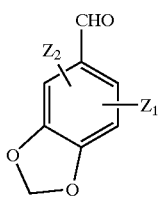

by treatment with a dialkyl malonate of Formula (16), wherein $R_{10}$ is $C_{1-8}$alkyl, $$CH_2(CO_2R_{10})_2 \quad (16)$$

in a solvent such as cyclohexane at reflux, in the presence of a base such as piperidine containing a catalytic amount of para-toluic acid, with removal of water using a Dean-Stark apparatus to afford a product of Formula (17).

(17)

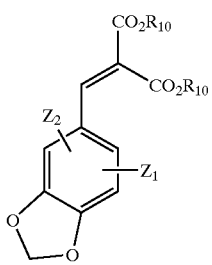

Reduction of a compound of Formula (17) with sodium borohydride in a solvent such as ethanol affords a product of Formula (18).

(18)

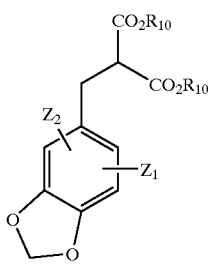

Mono saponification of an ester of Formula (18) with aqueous potassium hydroxide in a solvent such as ethanol followed by acidification with aqueous hydrochloric acid affords a malonic acid derivative of Formula (8), where $R_6$ is (b), A is —$CH_2$—, B is —O—, m is 1.

Reaction of an aldehyde of Formula (12) with a half acid of Formula (8) by the Knoevenagel procedure described above affords an acrylate of Formula (19).

(19)

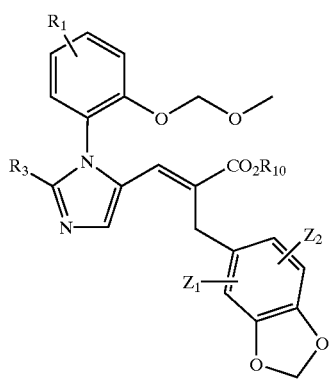

Deprotection of an ether of Formula (19) using ethanolic hydrogen chloride affords a phenol of Formula (20).

(20)

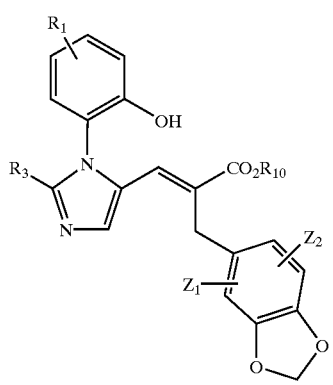

Alkylation of a phenol of Formula (20) using an allyl chloroacetate of Formula (21)

$$ClCH_2CO_2Allyl \quad (21)$$

in a solvent such as dimethylformamide using a base such as anhydrous potassium carbonate provides a mixed ester of Formula (22).

(22)

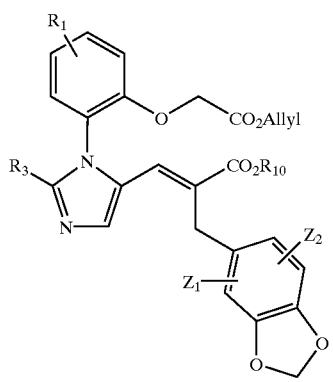

Selective cleavage of an allyl ester of Formula (22) using triethylsilane in the presence of a catalyst such as triphenylphosphine palladium(0) in a solvent such as dichloromethane provides a mono acid of Formula (23).

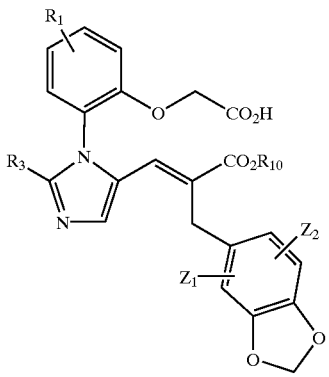
(23)

Coupling a mono acid of formula (23) with a sulfonamide of Formula (24)

 (24)

in the presence of a catalyst such as 4- dimethylaminopyridine and 1-ethyl-3-(3-dimethylaminopropyl)carbodiimide hydrochloride in a solvent such as dichloromethane at reflux affords a sulfonamide of Formula of (25).

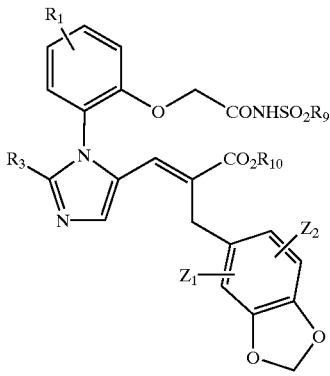
(25)

Saponification of an ester of Formula (25) using aqueous sodium hydroxide in a solvent such as ethanol affords, after acidification with aqueous hydrochloric acid, an acid of Formula (I), wherein $R_2$ is $OCH_2CO_2NHSO_2R_9$, A is —$CH_2$—, B is —O—, $R_4$ is hydrogen, and P is $CO_2H$.

Alternatively, a phenol of Formula (20) may by alkylated with chloroacetonitrile in a solvent such as dimethylformamide to produce a compound of Formula (26).

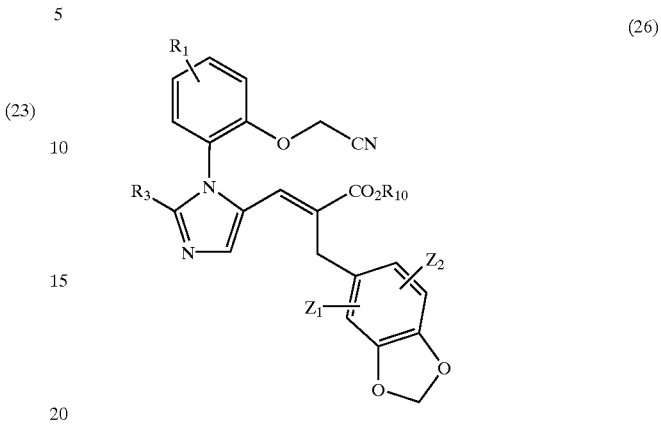
(26)

Reaction of a nitrile of Formula (26) with sodium azide in the presence of trimethyltin chloride in a solvent such as toluene at elevated temperature affords a tetrazole of Formula (27).

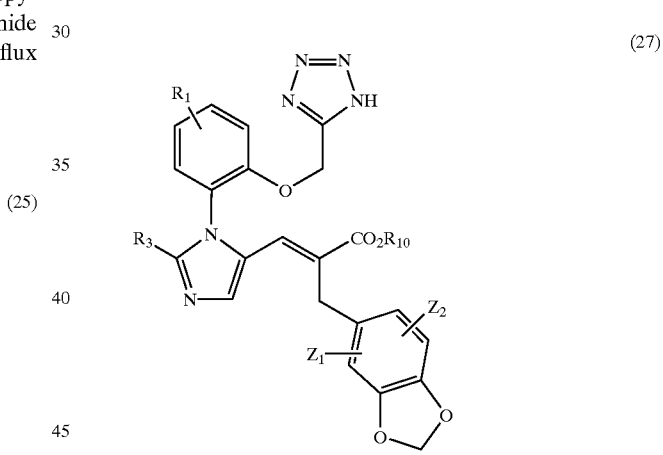
(27)

Saponification of an ester of Formula (27) using aqueous sodium hydroxide in a solvent such as ethanol affords, after acidification with aqueous hydrochloric acid, an acid of Formula (I), wherein $R_2$ is $OCH_2$(tetrazol-5-yl), A is —$CH_2$—, B is —O—, $R_4$ is hydrogen, and P is $CO_2H$.

Alternatively, a phenol of Formula (20) may also be alkylated with an alkyl halide of Formula (28), where X is I, Br, or Cl;

 (28)

to provide an ether of Formula (29).

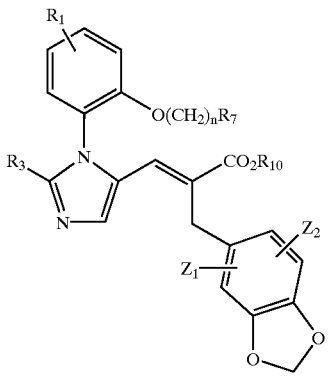

Saponification of an ester of Formula (29) using aqueous sodium hydroxide in a solvent such as ethanol affords, after acidification with aqueous hydrochloric acid, an acid of Formula (I), wherein $R_2$ is $O(CH_2)_nR_7$, A is —$CH_2$—, B is —O—, $R_4$ is hydrogen, P is $CO_2H$.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. Binding Assay

A) Membrane Preparation

Rat cerebellum or kidney cortex were rapidly dissected and frozen immediately in liquid nitrogen or used fresh. The tissues, 1–2 g for cerebellum or 3–5 g for kidney cortex, were homogenized in 15 mls of buffer containing 20 mM Tris HCl and 5 mM EDTA, pH 7.5 at 4° C. using a motordriven homogenizer. The homogenates were filtered through cheesecloth and centrifuged at 20,000×g for 10 minutes at 4° C. The supernatant was removed and centrifuged at 40,000×g for 30 minutes at 4° C. The resulting pellet was resuspended in a small volume of buffer containing 50 mM Tris, 10 mM $MgCl_2$, pH 7.5; aliquotted with small vials and frozen in liquid nitrogen. The membranes were diluted to give 1 and 5 mg of protein for each tube for cerebellum and kidney cortex in the binding assay.

Freshly isolated rat mesenteric artery and collateral vascular bed were washed in ice cold saline (on ice) and lymph nodes were removed from along the major vessel. Then, the tissue was homogenized using a polytron in buffer containing 20 mM Tris and 5 mM EDTA, pH 7.5 at 4° C. in 15 ml volume for ~6 gm of mesenteric artery bed. The homogenate was strained through cheesecloth and centrifuged at 2,000×g for 10 min. at 4° C. The supernatant was removed and centrifuged at 40,000×g for 30 min. at 4° C. The resulting pellet was resuspended as explained above for cerebellum and kidney cortex. Approximately 10 mg of membrane protein was used for each tube in binding experiments.

B) [$^{125}$I]ET-1 Binding Protocol

[$^{125}$I]ET-1 binding to membranes from rat cerebellum (2–5 mg protein/assay tube) or kidney cortex (3–8 mg protein/assay tube) were measured after 60 minutes incubation at 30° C. in 50 mM Tris HCl, 10 mM $MgCl_2$, 0.05% BSA, pH 7.5 buffer in a total volume of 100 ml. Membrane protein was added to tubes containing either buffer or indicated concentration of compounds. [$^{125}$I]ET-1 (2200 Ci/mmol) was diluted in the same buffer containing BSA to give a final concentration of 0.2–0.5 nM ET-1. Total and nonspecific binding were measured in the absence and presence of 100 nM unlabelled ET-1. After the incubation, the reactions were stopped with 3.0 ml cold buffer containing 50 mM Tris and 10 mM $MgCl_2$, pH 7.5. Membrane bound radioactivity was separated from free ligand by filtering through Whatman GF/C filter paper and washing the filters 5 times with 3 ml of cold buffer using a Brandel cell harvester. Filter papers were counted in a gamma counter with an efficiency of 75%.

II. In Vitro Vascular Smooth Muscle Activity

Rat aorta are cleaned of connective tissue and adherent fat, and cut into ring segments approximately 3 to 4 mm in length. Vascular rings are suspended in organ bath chambers (10 ml) containing Krebs-bicarbonate solution of the following composition (millimolar): NaCl, 112.0; KCl, 4.7; $KH_2PO_4$, 1.2; $MgSO_4$, 1.2; $CaCl_2$, 2.5; $NaHCO_3$, 25.0; and dextrose, 11.0. Tissue bath solutions are maintained at 37° C. and aerated continuously with 95% $O_2$/5% $CO_2$. Resting tensions of aorta are maintained at 1 g and allowed to equilibrate for 2 hrs., during which time the bathing solution is changed every 15 to 20 min. Isometric tensions are recorded on Beckman R-611 dynographs with Grass FT03 force-displacement transducer. Cumulative concentration-response curves to ET-1 or other contractile agonists are constructed by the method of step-wise addition of the agonist ET-1 concentrations are increased only after the previous concentration produces a steady-state contractile response. Only one concentration-response curve to ET-1 is generated in each tissue. ET receptor antagonists are added to paired tissues 30 min prior to the initiation of the concentration-response to contractile agonists.

ET-1 induced vascular contractions are expressed as a percentage of the response elicited by 60 mM KCl for each individual tissue which is determined at the beginning of each experiment. Data are expressed as the mean±S.E.M. Dissociation constants ($K_b$) of competitive antagonists were determined by the standard method of Arunlakshana and Schild.

The following examples are illustrative and are not limiting of the compounds of this invention.

EXAMPLE 1

(E)-3-[2-Butyl-1-[2-[N-(phenylsulfonyl)] carboxamido-4-methoxyphenyl]-1H-imidazol-5-yl]-2-[(2-methoxy-4,5-methylenedioxy)phenylmethyl]-2-propenoic Acid Dipotassium a) 2,4-Dimethoxynitrobenzene To a solution of sodium methoxide in methanol (freshly prepared by adding 50.0 g (2.17 mol) of sodium, in portions, to 1.5 l of methanol at 0° C.) was added 2,4-dichloronitrobenzene (95.0 g, 0.495 mol) in methanol (100 ml). After refluxing for 3 days, the reaction mixture was cooled in an ice bath and filtered, the precipitate was washed with water and dried ($Na_2SO_4$). The title compound was collected as a yellow solid (83.0 g, 91%).

b) 2-Hydroxy4-methoxynitrobenzene

To a solution of dimethoxynitrobenzene (30.0 g, 0.163 mol) in 99% methanesulfonic acid (300 ml) was added dl-methionine (31.8 g, 0.212 mol) and the mixture was stirred at rt for 24 h. The solution was poured onto ice and stirred with water (1.5 l). The precipitate was filtered and washed with water. The title compound was collected as a yellow solid (23.1 g, 84%).

c) 2-Methoxymethoxy-4-methoxynitrobenzene

To a solution of hydroxynitrobenzene (21.2 g, 0.125 mol) in DMF (250 ml) was added sodium hydride (4.5 g, 0.188 mol) at 0° C. under argon. The mixture was allowed to stir at 0° C. for 1 h, then bromomethyl methylether (22 ml, 0.150 mol) was added. After stirring for 18 h at rt the reaction was quenched with water. The mixture was extracted with ethyl acetate (3×30 ml) and the combined organic extracts were washed with brine and dried ($Na_2SO_4$). Removal of the solvent under reduce pressure gave the title compound as a brown oil (23.4 g, 88%).

d) 2-Methoxymethoxy-4-methoxy Aniline

To a solution of nitrobenzene (10.0 g, 0.047 mol) in ethanol (50 ml) was added 10% Pd/C (1.0 g) and the mixture was shaken under hydrogen atmosphere at 55 mm Hg for 24 h at rt. The mixture was filtered through a pad of Celite and the filtrate was dried ($Na_2SO_4$). Removal of the solvent afforded the title compound as a brown oil (8.2 g, 95%).

e) 1-Methoxypentaimidate Hydrochloride

To a solution of valeronitrile (72.3 g, 0.872 mol) in methanol (75 ml) was bubbled through gaseous HCl until saturation. The solution was then placed in the freezer for three days. The precipitate was filtered and was rinsed several times with ether. The title compound was collected as a white solid (130.0 g, 99%).

f) 1-Methoxypentaimidate

To a suspension of the HCl salt (16.5 g, 0.108 mol) in anhydrous ether (50 ml) was added triethylamine (15.5 ml, 0.110 mol). The mixture stirred at rt for 18 h under argon and then the precipitate was filtered. The filtrate was concentrated to 80% dryness and the crude product was used in the next reaction without further purification.

g) N-(2-Methoxymethoxy-4-methoxyphenyl)-pentanamidine

To a solution of 1-methoxypentaimidate (11.3 g, 0.109 mol) in dichloromethane (20 ml) was added freshly prepared 2-methoxymethoxy-4-methoxy aniline (10.0 g, 0.055 mol) of Example 1(d) and the mixture was stirred at reflux for 3 days. After removing the solvent flash chromatography of the residue (silica gel, 5% methanol/dichloromethane) afforded the title compound as a dark solid (11.7 g, 85%).

h) 2-Butyl-1-(2-methoxymethoxy-4-methoxyphenyl)-1H-imidazol-5-carboxaldehyde

To a solution of N-(2-Methoxymethoxy-4-methoxyphenyl)pentanamidine (5.10 g, 0.019 mol) in isopropanol (50 ml) was added triethylamine (3.20 ml, 0.0230 mol), acetic acid (1.4 ml, 0.025 mol) and 2-bromo-1,3-dicarboxaldehyde propane (3.20 g, 0.0211 mol), respectively. The mixture was stirred at reflux for 5 h and then cooled to room temperature. After filtration and concentration, The crude residue was dissolved in ethyl acetate and washed with 10% sodium bicarbonate solution, water, dried ($Na_2SO_4$). After removing the solvent under reduced pressure, flash chromatography of the residue (silica gel, 25% ethyl acetate/hexane) afforded the title compound as a dark yellow oil (3.85 g, 63%).

1-Methoxy-3,4-methylenedioxybenzene

To a solution of sesamol (10.0 g, 0.072 mol) in DMF (50 ml) was added sodium hydride (2.08 g, 0.087 mol) at rt under argon. After stirring for 1 h the mixture was treated with Iodomethane (13.5 ml, 0.216 mol) and stirred for another 18 h. Upon the removal of the solvent the residue was extracted with ethyl acetate and washed with water, dried ($Na_2SO_4$) and concentrated to afford the title compound as a dark brown oil (10.5 g, 96%).

j) 2-Methoxy-4,5-methylenedioxy Benzaldehyde

To a solution of phosphorous oxychloride (3.0 ml, 0.033 mol) in DMF (10 ml) was added a solution of 1-methoxy- 3,4-methylenedioxybenzene (2.0 g, 0.013 mol) in DMF (2 ml) at 0° C. After stirring at 60° C. for 18 h the mixture was cooled to 0° C. and then poured into water (500 ml). The precipitate was filtered and dried. The title compound was collected as a yellow solid (2.20 g, 92%).

k) Diethyl 2-(4,5-Methylenedioxy-1-methoxybenzylidene)-malonate

A solution of the 2-methoxy-4,5-methylenedioxy benzaldehyde (16.0 g, 0.089 mol), diethyl malonate (15.0 ml, 0.090 mol), piperidine (4.4 ml, 0.044 mol) and acetic acid (2.5 ml, 0.045 mol) in benzene (75 ml) stirred at reflux, equipped with a Dean-Stark apparatus, for 24 h. Upon removal of the solvent the crude residue was extracted with ethyl acetate and washed with 10% sodium carbonate solution, water, dried ($Na_2SO_4$). After removing the solvent, flash chromatography of the residue (silica gel, 25% ethyl acetate/hexane) provided the title compound as a yellow solid (26.0 g, 91%).

l) Diethyl 2-(4,5-Methylenedioxy-1-methoxybenzyl)-malonate

To a solution of the diethyl 2-(4,5-methylenedioxy-1-methoxybenylidene)-malonate (23.4 g, 0.073 mol) in ethanol (100 ml) was added sodium borohydride (2.8 g, 0.073 mol) and the mixture was stirred at rt for 5 h. The reaction was quenched with water and extracted with ethyl acetate (3×200 mL). The combined organic extracts were dried ($Na_2SO_4$) and evaporated to afford the title compound as an oil (20.3 g, 86%).

m) Ethyl Hydrogen 2-(4,5-Methylenedioxy-1-methoxybenyl)-malonate

To a solution of the diethyl 2-(4,5-methylenedioxy-1-methoxybenyl)-malonate (20.0 g, 0.066 mol) of in ethanol (50 ml) was added a solution of potassium hydroxide (3.5 g, 0.066 mol) in water (25 ml). The solution stirred at reflux for 6 h. After concentrating the aqueous layer was washed with ether and acidified with concentrated HCl to pH 1 and extracted with ethyl acetate. The organic extracts were dried ($Na_2SO_4$) and concentrated to afford the title compound as a yellow solid (17.3 g, 89%).

n) Ethyl-(E)-3-[2-butyl-1-(2-(methoxymethoxy)-4-methoxyphenyl]-1H-imidazol-5-yl]-2-[(2-methoxy-4,5-methylenedioxy)phenylmethyl]-2-propenoate A solution of 1-(2-methoxymethoxy-4-methoxyphenyl)-1H-imidazol-5-carboxaldehyde (1.00 g, 2.976 mmol) of Example 3(b), ethyl hydrogen 2-(4,5-methylenedioxy-1-methoxybenzyl)-malonate (2.64 g, 8.930 mmol), piperidine (0.15 ml, 1.488 mmol) and acetic acid (0.085 ml, 1.488 mmol) in benzene (50 ml) was equipped with a Dean-Stark apparatus, and stirred at reflux for 24 h. The solvent was removed and the crude residue was extracted with ethyl acetate and washed with 10% sodium carbonate solution, water, dried ($Na_2SO_4$). After removing the solvent flash chromatography of the residue (silica gel, 50% ethyl acetate/hexane) yielded the title compound as a brown oil (1.03 g, 63%). Anal. ($C_{30}H_{36}N_2O_8$) calcd: C, 65.18; H, 6.58; N, 5.07. found: C, 64.85; H, 6.20; N, 4.93.

o) Ethyl-(E)-3-[2-butyl-1-(2-hydroxy-4-methoxyphenyl)]-1H-imidazol-5-yl]-2-[(2-methoxy-4,5-methylenedioxyphenyl)methyl]-2-propenoate To a solution of the ethyl-(E)-3-[2-butyl-1-(2-(methoxymethoxy)-4-methoxyphenyl)]-1H-imidazol-5-yl]-2-[(2-methoxy-4,5-methylenedioxy)phenylmethyl]-2-propenoate (1.00 g, 1.811 mmol) in ethanol (25 ml) was added a catalytic amount of concentrated HCl. After stirring at reflux for 5 h the solvent was removed and the residue was extracted with ethyl acetate and washed with sodium bicarbonate (satd.), dried ($Na_2SO_4$). After removing the solvent flash chromatography of the residue (silica gel, 50% ethyl acetate/hexane) gave the title compound as a brown oil (0.856 g, 93%). Anal. ($C_{28}H_{32}N_2O_7$) calcd: C, 66.10; H, 6.36; N, 5.51. found: C, 65.92; H, 6.01; N, 5.12.

p) Ethyl-(E)-3-[2-butyl-1-(2-allylcarbomethoxy)-4-methoxyphenyl]-1H-imidazol-5-yl-2-[(2-methoxy-4,5-methylenedioxyphenyl)methyl]-2-propenoate To a solution of the ethyl-(E)-3-[2-butyl-1-(2-hydroxy-4-methoxyphenyl)]-1H-imidazol-5-yl]-2-[(2-methoxy-4,5-methylenedioxy)phenylmethyl]-2-propenoate (0.38 g, 0.776 mmol) in DMF (10 ml) was added sodium hydride (0.024 g, 0.996 mmol) and stirred at rt for 1 h under argon. Allyl chloroacetate (0.110 ml, 0.919 mmol) was added to the mixture and was allowed to stir for 18 h. The reaction was quenched with water and extracted with ethyl acetate. The organic extracts were washed with water, brine and dried ($Na_2SO_4$). After removing the solvent flash chromatography of the residue (silica gel, 50% ethyl acetate/hexane) afforded the title compound as a brown oil (0.426 g, 92%): MS (ESI) m/e 607.2 $[M+H]^+$.

q) Ethyl-(E)-3-[2-butyl-1-(2-carbomethoxy)-4-methoxyphenyl]-1H-imidazol-5-yl-2-[(2-methoxy-4,5-methylenedioxyphenyl)methyl]-2-propenoate To a solution of ethyl-(E)-3-[2-butyl-1-(2-allylcarbomethoxy)-4-methoxy-phenyl]-1H-imidazol-5-yl-2-[(2-methoxy-4,5-methylenedioxy)phenylmethyl]-2-propenoate (0.47 g, 0.791 mmol) in dichloromethane (10 ml) was added triethylsilane (0.70 ml, 4.384 mmol) and tetrakis(triphenylphosphine)palladium(0) (0.20 g, 0.175 mmol), respectively. After refluxing for 3 h, the reaction was quenched with water. The mixture was extracted with ethyl acetate (3×15 mL). The combined organic extracts were washed with brine and dried ($Na_2SO_4$). After removing the solvent, flash chromatography of the residue (silica gel, ethyl acetate) gave the title compound as a brown solid (0.400 g, 91%): Anal. ($C_{30}H_{34}N_2O_9$) calcd: C, 63.58; H, 6.06; N; 4.94. found: C, 63.21; H. 5.87; N, 4.63.

r) Ethyl-(E)-3-[2-Butyl-1-[2-[N-(phenylsulfonyl)]carboxamido-4-methoxyphenyl]-1H-imidazol-5-yl]-2-[(2-methoxy-4,5-methylenedioxyphenyl)methyl]-2-propenoate A solution of ethyl-(E)-3-[2-butyl-1-(2-carbomethoxy)-4-methoxyphenyl]-1H-imidazol-5-yl-2-[(2-methoxy-4,5-methylenedioxy)phenylmethyl]-2-propenoate (0.240 g, 0.379 mmol), 1-ethyl-3-(3-dimethylaminopropyl)-carbodiimide hydrochloride (0.087 g, 0.455 mmol), 4-dimethyl-aminopyridine (0.117 g, 0.955 mmol) and benzenesulfonamide (0.065 g, 0.417 mmol) in dichloromethane (25 ml) was allowed to stir at reflux for 5 h. The reaction was quenched with water and extracted with ethyl acetate. The organic extract was washed with brine and dried ($Na_2SO_4$). After removing the solvent, flash chromatography of the residue (silica gel, ethyl acetate) afforded the title compound as a yellow oil (0.192 g, 72%): Anal. ($C_{36}H_{39}N_3O_{10}S$) calcd: C, 61.25; H, 5.59; N, 5.96. found: C, 60.95; H, 5.25; N, 5.67.

s) (E)-3-[2-Butyl-1-[2-[N-(phenylsulfonyl)]carboxamido-4-methoxyphenyl]-1H-imidazol-5-yl]-2-[(2-methoxy-4,5-methylenedioxphenyl)methyl]-2-propenoic Acid To a solution of ethyl-(E)-3-[2-Butyl-1-[2-[N-(phenylsulfonyl)]carboxamido-4-methoxyphenyl]-1H-imidazol-5-yl]-2-[(2-methoxy-4,5-methylenedioxy)phenylmethyl]-2-propenoate (0.150 g, 0.213 mmol) in methanol (10 ml) was added a solution of potassium hydroxide (0.020 g, 0.319 mmol) in water (4 ml). The reaction was allowed to stir at reflux for 6 h. The organic solvent was removed and the aqueous layer was washed with ethyl acetate. The aqueous layer was acidified with concentrated HCl and extracted with ethyl acetate. The organic extract was washed with brine and dried (Na$_2$SO$_4$). After removing the solvent, crystallization of the residue from methanol afforded the title compound as a yellow solid (0.130 g, 91%): m.p. 155° C.; Anal. (C$_{34}$H$_{35}$N$_3$O$_9$S) calcd: C, 60.25; H, 5.22; N, 6.20. found: C, 60.11; H, 5.01; N, 5.92.

t) (E)-3-[2-Butyl-1-[2-[N-(phenylsulfonyl)]carboxamido-4-methoxyphenyl]-1H-imidazol-5-yl]-2-[(2-methoxy-4,5-methylenedioxy)phenylmethyl]-2-propenoic Acid Dipotassium A solution of the (E)-3-[2-butyl-1-[2-[N-(phenylsulfonyl)]carboxamido-4-methoxyphenyl]-1H-imidazol-5-yl]-2-[(2-methoxy-4,5-methylenedioxy)phenylmethyl]-2-propenoic acid (0.090 g, 0.133 mmol) in 95% ethanol (20 ml) was titrated with a solution of potassiun hydroxide (0.5 M) in 95% ethanol until pH 7.9 was obtained. The solvent was removed and dried in vacuum to afford the title compound as a light yellow solid (0.100 g, 99%): $^1$H NMR (400 MHz, d$_6$-DMSO) δ 7.72 (d, J=10 Hz, 2H), 7.39 (m, 3H), 7.05 (d, 1H), 6.89 (s, 1H), 6.72 (s, 1H), 6.55 (d, 2H), 6.42 (s, 1H), 6.35 (s, 1H), 5.92 (s, 2H), 4.26 (dd, J=10 Hz, 20 Hz, 2H), 3.81 (s, 3H), 3.72 (s, 3H), 3.65 (d, 2H), 1.48 (p, 2H), 1.21 (sextet, 2H), 0.80 (t, 3H); MS (ESI) m/e 678.2 [M+H]$^+$(free acid).

EXAMPLE 2

(E)-3-[2-Butyl-1-(2-benzyloxy-4-methoxy)phenyl-1H-imidazol-5-yl]-2-[(2-methoxy-4,5-methylenedioxyphenyl)methyl]-2-propenoic Acid a) Ethyl-(E)-3-[2-Butyl-1-(2-benzyloxy-4-methoxy)phenyl-1H-imidazol-5-yl]-2-[(2-methoxy-4,5-methylenedioxyphenyl)methyl]-2-propenoate To a solution of ethyl-(E)-3-[2-Butyl-1-(2-hydroxy-4-methoxy)phenyl-1H-imidazol-5-yl]-2-[(2-methoxy-4,5-methylenedioxyphenyl)methyl]-2-propenoate (0.176 g, 0.334 mmol) in DMF (8 ml) was added sodium hydride (0.027 g, 0.675 mmol) at 0° C. under argon, followed by benzyl bromide (0.048 ml, 0.401 mmol). After stirring for 1 h at rt the reaction was quenched with water. The mixture was extracted with ethyl acetate and the combined organic extracts were washed with brine and dried (Na$_2$SO$_4$). After removing the solvent, flash chromatography of the residue (silica gel, 1:1 hexane:ethyl acetate) afforded the title compound as an oil (0.044 g, 72%): $^1$H NMR (400 MHz, CDCl$_3$) δ 7.34–7.13 (mm, 7H), 7.10 (d, 1H), 6.65 (d, 1H), 6.60 (dd, 1H), 6.55 (s, 1H), 6.43 (s, 1H), 5.82 (s, 3H), 5.05 (s, 2H), 4.13 (q, 2H), 3.85 (s, 3H), 3.82 (s, 2H), 3.81 (s, 2H), 2.48 (m, 2H), 1.57 (m, 2H), 1.21 (sextet, 2H), 1.15 (t, 3H), 0.77 (t, 3H).

b) (E)-3-[2-Butyl-1-(2-benzyloxy-4-methoxy)phenyl-1H-imidazol-5-yl]-2-[(2-methoxy-4,5-methylenedioxyphenyl)methyl]-2-propenoic Acid To a solution of ethyl-(E)-3-[2-Butyl-1-(2-benzyloxy-4-methoxy)phenyl-1H-imidazol-5-yl]-2-(2-methoxy-4,5-methylenedioxyphenyl)methyl]-2-propenoate (0.140 g, 0.234 mol) in methanol (2 mL) was added 0.5 mL of 10% sodium hydroxide. The reaction was allowed to stir at reflux for 6 h. The organic solvent was removed and the aqueous layer was acidified with 6N HCl and extracted with ethyl acetate. The organic extract was washed with brine and dried (Na$_2$SO$_4$). After removing the solvent, flash chromatography of the residue (silica gel, 2:1 ethyl acetate:hexane) afforded the title compound as an off white solid (0.100 g, 75%): MS (ESI) m/e 571 [M+H]$^+$; mp: 215–216° C. (dec.); Anal. (C$_{33}$H$_{34}$N$_2$O$_7$.0.5H$_2$O) calcd. C, 68.38; H. 6.09; N, 4.83: found: C, 68.31; H, 6.00; N, 4.78.

EXAMPLE 3

(E)-3-[2-Butyl-1-[2-(2-picolyloxy)-4-methoxy]phenyl-1H-imidazol-5-yl]-2-[(2-methoxy-4,5-methylenedioxyphenyl)methyl]-2-propenoic Acid a) Ethyl-(E)-3-[2-Butyl-1-[2-(2-picolyl)oxy-4-methoxy]phenyl-1H-imidazol-5-yl]-2-[(2-methoxy-4,5-methylenedioxyphenyl)methyl]-2-propenoate To a solution of ethyl-(E)-3-[2-Butyl-1-(2-hydroxy-4-methoxy)phenyl-1H-imidazol-5-yl]-2-[(2-methoxy-4,5-methylenedioxyphenyl)methyl]-2-propenoate (0.100 g, 0.197 mmol) in DMF (5 mL) was added sodium hydride (0.024 g, 0.60 mmol) at 0° C. under argon, followed by 2-picolyl chloride hydrochloride (0.042 g, 0.256 mmol). After stirring for 16 h at rt the reaction was quenched with water. The mixture was extracted with ethyl acetate and the combined organic extracts were washed with brine and dried (Na$_2$SO$_4$). After removing the solvent, flash chromatography of the residue (silica gel, 1:2 hexane:ethyl acetate) afforded the title compound as an oil (0.035 g, 30%): $^1$H NMR (400 MHz, CDCl$_3$) δ 8.52 (d, 1H), 7.61 (t, 1H), 7.24–7.14 (m, 4H), 7.13 (d, 1H), 7.00 (d, 1H), 6.68 (d, 1H), 6.64 (dd, 1H), 6.55 (s, 2H), 6.43 (s, 2H), 5.82 (s, 2H), 5.14 (s, 2H), 4.10 (q, 2H), 3.87 (s, 3H), 3.84 (s, 5H), 2.45 (m, 2H), 1.57 (m, 2H), 1.22 (m, 2H), 1.14 (t, 3H), 0.77 (t, 3H).

b) (E)-3-[2-Butyl-1-[2-(2-picolyl)oxy-4-methoxy]phenyl-1H-midazol-5-yl]-2-[(2-methoxy-4,5-methylenedioxyphenyl)methyl]-2-propenoic Acid To a solution of ethyl (E)-3-[2-Butyl-1-[2-(2-picolyl)oxy-4-methoxy]phenyl-1H-imidazol-5-yl]-2-[(2-methoxy-4,5-methylenedioxyphenyl)methyl]-2-propenoate (0.035 g, 0.058 mmol) in methanol (2 mL) was added 1 ml of 10% sodium hydroxide. The reaction was allowed to stir at reflux for 6 h. The organic solvent was removed under reduced pressure and the aqueous layer was acidified with aqueous acetic acid and extracted with ethyl acetate. The organic extract was washed with brine and dried (Na$_2$SO$_4$). Removal the solvent under reduce pressure afforded the title compound as an oil (0.030 g, 91%): MS (ESI) m/e 572 [M+H]$^+$; mp: 220–222° C. (dec.); Anal. (C$_{32}$H$_{33}$N$_3$O$_7$.H$_2$O) calcd. C, 65.18; H, 5.98; N, 7.13: found C, 65.25, H, 5.93; N. 6.80.

EXAMPLE 4

(E)-3-[2-Butyl-1-[2-(tetrazol-5-yl)methoxy-4-methoxy]phenyl-1H-imidazol-5-yl]-2-[(2-methoxy-4,5-methylenedioxyphenyl)methyl]-2-propenoic Acid a) Ethyl-(E)-3-[2-Butyl-1-(2-cyanomethoxy-4-methoxy)phenyl-1H-imidazol-5-yl]-2-[(2-methoxy-4,5-methylenedioxyphenyl)methyl]-2-propenoate To a solution of ethyl-(E)-3-[2-Butyl-1-[2-hydroxy-4-methoxy]phenyl-1H-imidazol-5-yl]-2-[(2-methoxy-4,5-methylenedioxyphenyl)methyl]-2-propenoate (0.200 g, 0.403 mmol) in DMF (5 mL) was added sodium hydride (0.012 g, 0.484 mmol) at 0° C. under argon. The mixture was allowed to stir at room temperature for 1 h, then to it was added bromoacetonitrile (0.031 mL, 0.443 mmol) was added. After stirring for 24 h at rt the reaction was quenched with water. The mixture was extracted with ethyl acetate and the combined organic extracts were washed with brine and dried (Na$_2$SO$_4$). After removing the solvent, flash chromatography of the residue (silica gel, 1:1 hexane:ethyl acetate) afforded the title compound as a brown oil (0.198 g, 92%): $^1$H NMR (250 MHz, CDCl$_3$) δ 6.55 (s, 1H), 6.44 (s, 1H), 5.85 (s, 2H), 4.68 (s, 2H), 4.11 (q, 2H), 3.91 (s, 3H), 3.84 (s, 2H), 3.82 (s, 3H), 2.42 (m, 2H), 1.58 (quintet, 2H), 1.26 (m, 2H), 1.17 (t, 3H), 0.83 (t, 3H); MS (ESI) m/e 536.2 [M+H]$^+$.

b) Ethyl-(E)-3-[2-[2-Butyl-1-[2-(tetrazol-5-yl)methoxy-4-methoxy]phenyl-1H-imidazol-5-yl]-2-[(2-methoxy-4,5-methylenedioxyphenyl)methyl]-2-propenoate To a solution of sodium azide (0.061 g, 0.935 mmol) and trimethyltin chloride (0.150 g, 0.748 mmol) in toluene (10 mL) was added ethy-(E)-3-[2-Butyl-1-(2-cyanomethoxy-4-methoxy)phenyl-1H-imidazol-5-yl]-2-[(2-methoxy-4,5-methylenedioxyphenyl)methyl]-2-propenoate at room temperature. The mixture was stirred at reflux for 24 h. The reaction was cooled to room temperature then treated with a solution of methanolic 1N HCl (2 mL). The mixture was extracted with ethyl acetate and the combined organic extract were washed with brine and dried ($Na_2SO_4$). After removing the solvent under reduced pressure, flash chromatography of the residue (silica gel, ethyl acetate) afforded the title compound as a brown solid (0.080 g, 72%): $^1$H NMR (250 MHz, $CDCl_3$) δ 7.17–7.07 (m, 3H), 6.97 (d, 1H), 6.72 (dd, 1H), 6.66 (s, 1H), 6.35 (s, 1H), 5.83 (s, 2H), 5.32 (dd, 2H), 4.10 (q, 2H), 3.92 (s, 3H), 3.83 (s, 3H), 3.74 (s, 2H), 2.36 (mm, 2H), 1.44 (quintet, 2H), 1.16 (m, 5H), 0.75 (t, 3H); MS (ESI) m/e 591.2 [M+H]$^+$; mp: 140–144° C.

c) (E)-3-[2-Butyl-1-[2-(tetrazol-5-yl)methoxy-4-methoxy]phenyl-1H-imidazol-5-yl]-2-[(2-methoxy-4,5-methylenedioxyphenyl)methyl]-2-propenoic Acid To a solution of ethyl-(E)-3-[2-Butyl-1-[2-(tetrazol-5-yl)methoxy-4-methoxy]phenyl-1H-imidazol-5-yl]-2-[(2-methoxy-4,5-methylenedioxyphenyl)methyl]-2-propenoate (0.100 g, 0.169 mmol) in methanol (5 mL) was added 3 ml of 1N sodium hydroxide. The reaction mixture was allowed to stir at reflux for 2 h. The organic solvent was removed and the aqueous layer was acidified with concentrated HCl and extracted with ethyl acetate. The organic extract was washed with brine and dried ($Na_2SO_4$). Removal of the solvent under reduce pressure afforded the title compound as a brown solid (0.078 g, 82%): MS (ESI) m/e 563.2 [M+H]$^+$; mp: 208–210° C.; Anal. ($C_{28}H_{30}N_6O_7$) calcd. C, 59.72; H, 5.38; N, 14.93: found C, 59.38; H, 5.26; N, 14.72.

EXAMPLE 5

(E)-3-[2-Butyl-1-[2-(2-carboxyphenyl)methoxy-4-methoxy]phenyl-1H-imidazol-5-yl]-2-[(2-methoxy-4,5-methylenedioxyphenyl)methyl]-2-propenoic Acid a) Ethyl-(E)-3-[2-Butyl-1-[2-(2-carboxyphenyl)methoxy-4-methoxy]phenyl-1H-imidazol-5-yl]-2-[(2-methoxy-4,5-methylenedioxyphenyl)methyl]-2-propenoate To a solution of ethyl-(E)-3-[2-Butyl-1-(2-hydroxy-4-methoxy)phenyl-1H-imidazol-5-yl]-2-[(2-methoxy-4,5-methylenedioxyphenyl)methyl]-2-propenoate (0.100 g, 0.197 mmol) in DMF (5 mL) was added sodium hydride (0.024 g, 0.60 mmol) at 0° C. under argon, followed by methyl o-bromomethyl benzoate (0.042 g, 0.256 mmol). After stirring for 2 h at 0° C. the reaction was quenched with water. The mixture was extracted with ethyl acetate and the combined organic extracts were washed with brine and dried ($Na_2SO_4$). After removing the solvent, flash chromatography of the residue (silica gel, 1:2 hexane:ethyl acetate) afforded the title compound as an oil (0.035 g, 30%): $^1$H NMR (400 MHz, $CDCl_3$) δ 8.52 (d, 1H), 7.61 (t, 1H), 7.24–7.14 (m, 4H), 7.13 (d, 1H), 7.00 (d, 1H), 6.68 (d, 1H), 6.64 (dd, 1H), 6.55 (s, 2H), 6.43 (s, 2H), 5.82 (s, 2H), 5.14 (s, 2H), 4.10 (q, 2H), 3.87 (s, 3H), 3.84 (s, 5H), 2.45 (m, 2H), 1.57 (m, 2H), 1.22 (m, 2H), 1.14 (t, 3H), 0.77 (t, 3H).

h) E)-3-[2-Butyl-1-[2-(2-carboxyphenyl)methoxy-4-methoxy]phenyl-1H-imidazol-5-yl]-2-[(2-methoxy-4,5-methylenedioxyphenyl)methyl]-2-propenoic Acid To a solution of ethyl (E)-3-[2-Butyl-1-[2-(2-carboxyphenyl)methoxy-4-methoxy]phenyl-1H-imidazol-5-yl]-2-[(2-methoxy-4,5-methylenedioxyphenyl)methyl]-2-propenoate (0.035 g, 0.058 mmol) in methanol (2 mL) was added 1 ml of 10% sodium hydroxide. The reaction was allowed to stir at reflux for 6 h. The organic solvent was removed under reduced pressure and the aqueous layer was acidified with aqueous acetic acid and extracted with ethyl acetate. The organic extract was washed with brine and dried ($Na_2SO_4$). Removal the solvent under reduce pressure afforded the title compound as an oil (0.030 g, 91%): MS (ESI) m/e 572 [M+H]$^+$; mp: 220–222° C. (dec.); Anal. ($C_{32}H_{33}N_3O_7.H_2O$) calcd. C, 65.18; H, 5.98; N, 7.13. found C, 65.25, H. 5.93; N, 6.80.

EXAMPLE 6

E-3-[2-Butyl-1-[2-(2-ethyl-2H-tetrazol-5-yl)methoxy-4-methoxy]phenyl-1H-imidazol-5-yl]-2-[(2-methoxy-4,5-methylenedioxyphenyl)methyl]-2-propenoic Acid a) Ethyl-(E)-3-[2-Butyl-1-[2-(2-ethyl-2H-tetrazol-5-yl)methoxy-4-methoxy]phenyl-1H-imidazol-5-yl]-2-[(2-methoxy-4,5-methylenedioxyphenyl)methyl]-2-propenoate To a solution of ethyl-(E)-3-[2-Butyl-1-[2-(tetrazol-5-yl)methoxy-4-methoxyphenyl-1H-imidazol-5-yl]-2-[(2-methoxy-4,5-methylenedioxyphenyl)methyl]-2-propenoate (0.100 g, 17.30 mmol) in DMF (10 mL) was added sodium hydride (5 mg, 0.225 mmol) followed by ethyl iodide (16 μL, 0.20 mmol). The reaction mixture was allowed to stir at room temperature for 18 h and quenched with water. The mixture was extracted with 1:1 hexane/ethyl acetate and the organic extract was washed with brine and dried ($Na_2SO_4$). After removing the solvent, column chromatography of the residue with 1:1 hexane/ethyl acetate afforded the title compound as an oil (92 mg, 86%): $^1$H NMR (250 MHz, $CDCl_3$) δ 0.80 (t, 3H), 1.15 (t, 3H), 1.6 (m, 2H), 1.65 (t, 3H), 2.40 (m, 2H), 3.82 (s, 3H), 3.83 (d, 2H), 3.88 (s, 3H), 4.15 (q, 2H), 4.57 (q, 2H), 5.22 (s, 2H), 5.82 (s, 2H), 6.44 (s, 1H), 6.52 (s, 1H), 6.62 (dd, 1H), 6.85 (d, 1H), 7.00–7.30 (m, 3H);

To a solution of ethyl-(E)-3-[2-Butyl-1-[2-(N-ethyltetrazol-5-yl)methoxy-4-methoxy]phenyl-1H-imidazol-5-yl]-2-[(2-methoxy-4,5-methylenedioxyphenyl)methyl]-2-propenoate (0.15 g, 0.25 mmol) in methanol (5 mL) was added 3 mL of 1N sodium hydroxide. The reaction mixture was allowed to stir at reflux for 4 h. The reaction mixture was washed with diethyl ether and the aqueous layer was acidified with concentrated HCl and extracted with ethyl acetate. The organic extract was washed with brine and dried ($Na_2SO_4$). After removing the solvent, reverse phase HPLC of the residue eluting with 40% $CH_3CN/H_2O$ containing 1% TFA afforded the title compound as a brown solid (0.13 g, 91%): MS (ESI) m/e [M+H]$^+$591; mp: 189–193° C.; Anal. ($C_{28}H_{30}N_6O_7.9/4CF_3COOH$) calcd. C, 48.97; H, 4.20; N, 9.93. found C, 49.20; H, 4.42; N, 10.21.

EXAMPLE 7

E-3-[2-Butyl-1-[2-(3-picolyl)oxy-4-methoxy]phenyl-1H-imidazol-5-yl]-2-[(2-methoxy-4,5-methylenedioxyphenyl)methyl]-2-propenoic Acid Acetate Salt m.p. 181–183° C. (dec).

EXAMPLE 8

E-3-[2-Butyl-1-[2-(3-carboxyphenyl)methoxy-4-methoxy]phenyl-1H-imidazol-5-yl]-2-[(2-methoxy-4,5-methylenedioxyphenyl)methyl]-2-propenoic Acid m.p. 127–129° C. (dec).

EXAMPLE 9

E-3-[2-Butyl-1-[2-(N-methyl)carboamidomethoxy-4-methoxy]phenyl-1H-imidazol-5-yl]-2-[(2-methoxy-4,5-methylenedioxyphenyl)methyl]-2-propenoic Acid m.p. 129–131° C.

EXAMPLE 10

E-3-[2-Butyl-1-(2-hydroxyethyloxy-4-methoxy) phenyl-1H-imidazol-5-yl]-2-[(2-methoxy-4,5-methylenedioxyphenyl)methyl]-2-propenoic Acid m.p. 108–110° C.

EXAMPLE 11

E-3-[2-Butyl-1-[2-[N-(4-isopropylphenyl)sulfonyl] carboxamidomethoxy-4-methoxy]phenyl-1H-imidazol-5-yl]-2-[(2-methoxy-4,5-methylenedioxyphenyl)methyl]-2-propenoic Acid m.p. 144–146° C.

EXAMPLE 12

E-3-[2-Butyl-1-[2-[N-(2-methylphenyl)sulfonyl] carboxamidomethoxy-4-methoxy]phenyl-1H-imidazol-5-yl]-2-[(2-methoxy-4,5-methylenedioxyphenyl)methyl]-2-propenoic Acid m.p. 146–148° C.

EXAMPLE 13

E-3-[2-Butyl-1-[2-(N-dimethylaminosulfonyl) carboxamidomethoxy-4-methoxy]phenyl-1H-imidazol-5-yl]-2-[(2-methoxy-4,5-methylenedioxyphenyl)methyl]-2-propenoic Acid m.p. 118–120° C.

EXAMPLE 14

E-3-[2-Butyl-1-[2-(N-methanesulfonyl) carboxamidomethoxy-4-methoxy]phenyl-1H-imidazol-5-yl]-2-[(2-methoxy-4,5-methylenedioxyphenyl)methyl]-2-propenoic Acid m.p. 135–137° C.

EXAMPLE 15

E-3-[2-Butyl-1-[2-(N-phenylcarbonyl) carboxamidomethoxy-4-methoxy]phenyl-1H-imidazol-5-yl]-2-[(2-methoxy-4,5-methylenedioxyphenyl)methyl]-2-propenoic Acid m.p. 89–91° C.

EXAMPLE 16

E-3-[2-Butyl-1-[2-(2-tolulyl)oxy-4-methoxy]phenyl-1H-imidazol-5-yl]-2-[(2-methoxy-4,5-methylenedioxyphenyl)methyl]-2-propenoic Acid m.p. 228–229° C.

EXAMPLE 17

E-3-[2-Butyl-1-[2-(N-t-butylsulfonyl) carboxamidomethoxy-4-methoxy]phenyl-1H-imidazol-5-yl]-2-[(2-methoxy-4,5-methylenedioxyphenyl)methyl]-2-2propenoic Acid m.p. 142–144° C.

EXAMPLE 18

E-3-[2-Butyl-1-[2-(2-(tetrazol-5-yl)benzyloxy-4-methoxy]phenyl-1H-imidazol-5-yl]-2-[(2-methoxy-4,5-methylenedioxyphenyl)methyl]-2-propenoic Acid m.p. 199–205° C.

EXAMPLE 19

(E)-3-[2-Butyl-1-(2-(2,4-difluorobenzyloxy)-4-methoxy)phenyl-1H-imidazol-5-yl]-2-[(2-methoxy-4,5-methylenedioxyphenyl)methyl]-2-propenoic Acid m.p. 198–201° C.

EXAMPLE 20

(E)-3-[2-Butyl-1-(2-(4-fluorobenzyloxy)-4-methoxy) phenyl-1H-imidazol-5-yl]-2-[(2-methoxy-4,5-methylenedioxyphenyl)methyl]-2-propenoic Acid m.p. 204–206° C.

EXAMPLE 21

(E)-3-[2-Butyl-1-[2-(5-chlorothiophen-5-yl) methoxy-4-methoxy]phenyl-1H-imidazol-5-yl]-2-[(2-methoxy-4,5-methylenedioxyphenyl)methyl]-2-propenoic Acid m.p. 188–189° C.

EXAMPLE 22

E-3-[2-Butyl-1-[2-(2-ethyl-2H-tetrazol-5-yl) benzyloxy-4-methoxyphenyl]-1H-imidazol-5-yl]-2-[(2-methoxy-4,5-methylenedioxyphenyl)methyl]-2-propenoic Acid m.p. 175–181° C.

EXAMPLE 23

(E)-3-[2-Butyl-1-[2-(1-ethyl-1H-tetrazol-5-yl) methoxy-4-methoxyphenyl]-1H-imidazol-5-yl]-2-[(2-methoxy-4,5-methylenedioxyphenyl)methyl]-2-propenoic Acid m.p. 185–190° C.

EXAMPLE 24

(E)-3-[2-Butyl-1-[2-(2-propyl-2H-tetrazol-5-yl) methoxy-4-methoxyphenyl]-1H-imidazol-5-yl]-2-[(2-methoxy-4,5-methylenedioxyphenyl)methyl]-2-propenoic Acid m.p. 110–118° C.

EXAMPLE 25

(E)-3-[2-Butyl-[1-(2-carboxymethoxy)-4-methoxy) phenyl-1H-imidazol-5-yl]-2-[(2-methoxy-4,5-methylenedioxyphenyl)methyl]-2-propenoic Acid a) Ethyl-(E)-3-[2-butyl-1-(2-(methoxymethoxy)-4-methoxyphenyl)]-1H-imidazol-5-yl]-2-[(2-methoxy-4,5-methylenedioxy)phenylmethyl]-2-propenoate A solution of 1-(2-methoxymethoxy-4-methoxyphenyl)-1H-imidazol-5-carboxaldehyde (1.00 g, 2.976 mmol) of Example 3(b), ethyl hydrogen 2-(4,5-methylenedioxy-1-methoxybenzyl)-malonate (2.64 g, 8.930 mmol), piperidine (0.15 ml, 1.488 mmol) and acetic acid (0.085 ml, 1.488 mmol) in benzene (50 ml) was equipped with a Dean-Stark apparatus, and stirred at reflux for 24 h. The solvent was removed and the crude residue was extracted with ethyl acetate and washed with 10% sodium carbonate solution, water, dried ($Na_2SO_4$). After removing the solvent flash chromatography of the residue (silica gel, 50% ethyl acetate/hexane) yielded the title compound as a brown oil (1.03 g, 63%). Anal. ($C_{30}H_{36}N_2O_8$) calcd: C, 65.18; H, 6.58; N, 5.07. found: C, 64.85; H, 6.20; N, 4.93.

b) Ethyl-(E)-3-[2-butyl-1-(2-hydroxy-4-methoxyphenyl)-1H-imidazol-5-yl]-2-[(2-methoxy-4,5-methylenedioxyphenyl)methyl]-2-propenoate To a solution of the ethyl-(E)-3-[2-butyl-1-(2-(methoxymethoxy)-4-methoxyphenyl)]-1H-imidazol-5-yl]-2-[(2-methoxy-4,5-methylenedioxy)phenylmethyl]-2-propenoate (1.00 g, 1.811 mmol) in ethanol (25 ml) was added a catalytic amount of concentrated HCl. After stirring at reflux for 5 h the solvent was removed and the residue was extracted with ethyl acetate and washed with sodium bicarbonate (satd.), dried ($Na_2SO_4$). After removing the solvent flash chromatography of the residue (silica gel, 50% ethyl acetate/hexane) gave the title compound as a brown oil (0.856 g, 93%). Anal. ($C_{28}H_{32}N_2O_7$) calcd: C, 66.10; H, 6.36; N, 5.51. found: C, 65.92; H, 6.01; N, 5.12.

c) Ethyl-(E)-3-[2-butyl-1-(2-allylcarbomethoxy)-4-methoxyphenyl]-1H-imidazol-5-yl-2-[(2-methoxy-4,5-methylenedioxyphenyl)methyl]-2-propenoate To a solution of the ethyl-(E)-3-[2-butyl-1-(2-hydroxy-4-methoxyphenyl)]-1H-imidazol-5-yl]-2-[(2-methoxy-4,5-methylenedioxyphenylmethyl]-2-propenoate (0.38 g, 0.776 mmol) in DMF (10 ml) was added sodium hydride (0.024 g, 0.996 mmol) and stirred at rt for 1 h under argon. Allyl chloroacetate (0.110 ml, 0.919 mmol) was added to the mixture and was allowed to stir for 18 h. The reaction was quenched with water and extracted with ethyl acetate. The organic extracts were washed with water, brine and dried ($Na_2SO_4$). After removing the solvent flash chromatography of the residue (silica gel, 50% ethyl acetate/hexane) afforded the title compound as a brown oil (0.426 g, 92%): MS (ESI) m/e 607.2 [M+H]$^+$.

d) Ethyl-(E)-3-[2-butyl-1-(2-carbomethoxy)-4-methoxyphenyl]-1H-imidazol-5-yl-2-[(2-methoxy-4,5-methylenedioxyphenyl)methyl]-2-propenoate To a solution of ethyl-(E)-3-[2-butyl-1-(2-allylcarbomethoxy)-4-methoxy-phenyl]-1H-imidazol-5-yl-2-[(2-methoxy-4,5-methylenedioxy)phenylmethyl]-2-propenoate (0.47 g, 0.791 mmol) in dichloromethane (10 ml) was added triethylsilane (0.70 ml, 4.384 mmol) and tetrakis(triphenylphosphine)palladium(0) (0.20 g, 0.175 mmol), respectively. After refluxing for 3 h, the reaction was quenched with water. The mixture was extracted with ethyl acetate (3×15 mL). The combined organic extracts were washed with brine and dried ($Na_2SO_4$). After removing the solvent, flash chromatography of the residue (silica gel, ethyl acetate) gave the title compound as a brown solid (0.400 g, 91%): Anal. ($C_{30}H_{34}N_2O_9$) calcd: C, 63.58; H, 6.06; N, 4.94. found: C, 63.21; H, 5.87; N, 4.63.

e) (E)-3-[2-Butyl-[1-[2-(carbomethoxy)-4-methoxyphenyl]-1H-imidazol-5-yl]-2-[(6-methoxy-3,4-methylenedioxyphenyl)methyl]-2-propenoic Acid To a solution of ethyl-(E)-3-[2-butyl-1-(2-carbomethoxy)-4-methoxyphenyl]-1H-imidazol-5-yl-2-[(2-methoxy-4,5-methylenedioxy)phenylmethyl]-2-propenoate (0.50 g, 0.902 mmol) in methanol (10 ml) was added a solution of potassium hydroxide (0.065 g, 1.170 mmol) in water (4 ml). The reaction was allowed to stir at reflux for 6 h. The organic solvent was removed and the aqueous layer was washed with ether. The aqueous layer was acidified with concentrated HCl and extracted with ethyl acetate. The combined organic extracts were dried ($Na_2SO_4$) and evaporated to afford a white solid. Crystallization from methanol yielded the title compound as a white solid (0.456 g, 94%): $^1$H NMR (400 MHz, d$_6$-DMSO) δ 7.22 (d, J=10 Hz, 1H), 7.10 (s, 1H), 6.89 (s, 1H), 6.73 (d, 2H), 6.29 (s, 1H), 5.91 (s, 2H), 4.76 (dd, J=8 Hz, 20 Hz, 2H), 3.84 (s, 3H), 3.82 (s, 3H), 3.65 (s, 2H), 2.48 (m, 2H), 1.51 (p, 2H), 1.18 (sextet, 2H), 0.76 (t, 3H); MS (ESI) m/e 539.2 [M+H]$^+$; mp: 164° C., Anal. ($C_{28}H_{30}N_2O_9$) calcd: C, 62.43; H, 5.63; N, 5.20. found: C, 62.10; H, 5.32; N, 4.19.

EXAMPLE 26

E-3-[2-Butyl-1-[2-(3-carboxy)propoxy-4-methoxy]phenyl-1H-imidazol-5-yl]-2-[(2-methoxy-4,5-methylenedioxyphenyl)methyl]-2-propenoic Acid m.p. 128–130° C.

EXAMPLE 27

E-3-[1-(2-Carboxymethoxy-4-methoxy)phenyl-2-isopropyl-1H-imidazol-5-yl]-2-[(2-methoxy-4,5-methylenedioxyphenyl)methyl]-2-propenoic Acid m.p. 256–258° C.

EXAMPLE 28

E-3-[1-(2-Carboxymethoxy-4-methoxy)phenyl-2-isobutyl-1H-imidazol-5-yl]-2-[(2-methoxy-4,5-methylenedioxyphenyl)methyl]-2-propenoic Acid m.p. 264–266° C.

EXAMPLE 29

E-3-[1-(2-Carboxymethoxy-4-methoxy)phenyl-2-(1-methyl)propyl-1H-imidazol-5-yl]-2-[(2-methoxy-4,5-methylenedioxyphenyl)methyl]-2-propenoic Acid m.p. 252–253° C.

EXAMPLE 30

E-3-[2-Butyl-1-(2-carboxymethoxy-4-methoxy)pheny)-1H-imidazol-5-yl]-2-[(3-methoxy-4,5-methylenedioxyphenyl)methyl]-2-propenoic Acid m.p. 179–179.50° C.

EXAMPLE 31

E-3-[2-Butyl-1-(2-carboxymethoxy-4-methoxy)pheny)-1H-imidazol-5-yl]-2-[(3,4-methylenedioxyphenyl)methyl]-2-propenoic Acid m.p. 157–158° C.

EXAMPLE 32

E-3-[2-Butyl-1-(2-carboxymethoxy-4-methoxy)phenyl-1H-imidazol-5-yl]-2-[(2-chloro-4,5-methylenedioxyphenyl)methyl]-2-propenoic Acid m.p. 228–230° C.

EXAMPLE 33

E-3-[2-Butyl-1-(2-carboxymethoxy-4-methoxy)
phenyl-1H-imidazol-5-yl]-2-[(2-ethoxy-4,5-
methylenedioxyphenyl)methyl]-2-propenoic Acid m.p. 131–133° C.

EXAMPLE 34

E-3-[2-Butyl-1-(2-carbomethoxy-4-methoxy)pheny)-
1H-imidazol-5-yl]-2-[(4-methoxyphenyl)methyl]-2-
propenoic Acid m.p. 128–130° C.

EXAMPLE 35

E-3-[2-Butyl-1-(2-carbomethoxy-4-methoxy)phenyl-
1H-imidazol-5-yl]-2-[(4,5-dimethoxyphenyl)
methyl]-2-propenoic Acid

M.P. 135–138° C.

EXAMPLE 36

E-3-[2-Butyl-1-(2-carbomethoxy-4-methoxy)phenyl-
1H-imidazol-5-yl]-2-[(2,4-dimethoxyphenyl)
methyl]-2-propenoic Acid m.p. 145–147° C.

EXAMPLE 37

E-3-[2-Butyl-1-(2-carbomethoxy-4-methoxy)phenyl-
1H-imidazol-5-yl]-2-[(3-methoxyphenyl)methyl]-2-
propenoic Acid m.p. 146–148° C.

EXAMPLE 38

E-3-[2-Butyl-1-(2-carbomethoxy-4-methoxy)phenyl-
1H-imidazol-5-yl]-2-[(3-hydroxyphenyl)methyl]-2-
propenoic Acid m.p. 129–131° C.

EXAMPLE 39

E-3-[2-Butyl-1-(2-carbomethoxy-4-methoxy)phenyl-
1H-imidazol-5-yl]-2-[(4-hydroxyphenyl)methyl]-2-
propenoic Acid m.p. 135–137° C.

EXAMPLE 40

E-3-[2-Butyl-1-(2-carbomethoxy-4-methoxy)phenyl-
1H-imidazol-5-yl]-2-[(2-hydroxy-4-methoxyphenyl)
methyl]-2-propenoic Acid m.p. 140–143° C.

EXAMPLE 41

E-3-[2-Butyl-1-(2-carbomethoxy-4-methoxy)phenyl-
1H-imidazol-5-yl]-2-(3,4-difluorophenyl)methyl-2-
propenoic Acid m.p. 114–115° C.

EXAMPLE 42

E-3-[2-Butyl-1-(2-carbomethoxy-4-methoxy)phenyl-
1H-imidazol-5-yl]-2-(3,4-dichlorophenyl)methyl-2-
propenoic Acid Dicyclohexyl Amine Salt m.p. 113–114° C.

EXAMPLE 43

E-3-[2-Butyl-1-(2-carbomethoxy-4-methoxy)phenyl-
1H-imidazol-5-yl]-2-(indol-6-yl)methyl-2-propenoic
Acid m.p. 161–162° C.

EXAMPLE 44

E-3-[2-Butyl-1-(2-carbomethoxy-4-methoxy)phenyl-
1H-imidazol-5-yl]-2-(indol-5-yl)methyl-2-propenoic
Acid m.p. 165–167° C.

EXAMPLE 45

E-3-[2-Butyl-1-(2-carbomethoxy-4-methoxy)phenyl-
1H-imidazol-5-yl]-2-[2,2-dimethyl-(1,3-benzodiox-
5-yl)methyl]-2-propenoic Acid m.p. 124–127° C.

EXAMPLE 46

E-3-[2-Butyl-1-(2-carbomethoxy-4-methoxy)phenyl-
1H-imidazol-5-yl]-2-(phenylmethyl)-2-propenoic
Acid m.p. 128–130° C.

EXAMPLE 47

Formulations for pharmaceutical use incorporating compounds of the present invention can be prepared in various forms and with numerous excipients. Examples of such formulations are given below.

Inhalant Formulation

A compound of Formula I, (1 mg to 100 mg) is aerosolized from a metered dose inhaler to deliver the desired amount of drug per use.

| Tablets/Ingredients | Per Tablet |
|---|---|
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
| | 2.3 mg |

Procedure for Tablets:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then steriled by filtration through a 0.22 micron membrane filter and sealed in sterile containers.

What is claimed is:

1. A compound of Formula (I):

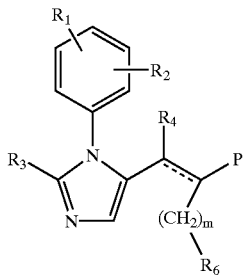

wherein:
$R_1$ is H or $C_{1-3}$alkoxy;
$R_2$ is —$(CH_2)_xC(O)NHS(O)_2R_9$, —$OR_5$, —$O(CH_2)_{1-3}CO_2H$ or —$(CH_2)_nR_7$;
$R_3$ is $C_{1-5}$alkyl;
$R_4$ is hydrogen;
$R_5$ is —$(CH_2)_xC(O)NHS(O)_2R_9$, —$(CH_2)_xC(O))NHC(O)R_9$, —$(CH_2)_nR_7$ or pyridyl
which may be unsubstituted or substituted by $Z_1$;
$R_6$ is a moiety of formula (b),

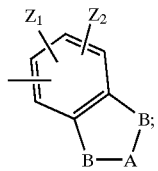

P is $CO_2H$;
$R_7$ is hydroxy, —$NHSO_2R_9$, —$CONH(C_{1-5}alkyl)$, or $R_7$ is tetrazol-5-yl or piperazinyl, both of which may be unsubstituted or substituted by $C_{1-6}$alkyl, or $R_7$ is thienyl, pyridyl, pyrimidyl, or phenyl, all of which may be unsubstituted or substituted by one or more $Z_1$ or $Z_2$ groups;
$R_9$ is $C_{1-5}$alkyl, $N(C_{1-5}alkyl)_2$ or $R_9$ is phenyl which may be unsubstituted or substituted by $C_{1-5}$alkyl;
n is 1 to 4;
m is 1;
x is 0 to 4;
$Z_1$ and $Z_2$ are independently hydrogen, hydroxy, $C_{1-6}$alkoxy, $CO_2H$, $C(O)NH_2$, F, Cl, or tetrazolyl which may be unsubstituted or substituted by $C_{1-6}$alkyl;
A is —$CH_2$—; and B is —O—;
and the dotted line indicates the presence of a double bond;
or a pharmaceutically acceptable salt thereof.

2. A compound of claim 1 chosen from the group consisting of:
(E)-3-[2-Butyl-1-[2-(tetrazol-5-yl)methoxy-4-methoxy]phenyl-1H-imidazol-5-yl]-2-[(2-methoxy-4,5-methylenedioxyphenyl)methyl]-2-propenoic acid;
(E)-3-[2-Butyl-1-[2-(4-carboxyphenyl)methoxy-4-methoxy]phenyl-1H-imidazol-5-yl]-2-[(2-methoxy-4,5-methylenedioxyphenyl)methyl]-2-propenoic acid;
E-3-[2-Butyl-1-[2-(3-carboxyphenyl)methoxy-4-methoxy]phenyl-1H-imidazol-5-yl]-2-[(2-methoxy-4,5-methylenedioxyphenyl)methyl]-2-propenoic acid;
E-3-[2-Butyl-1-[2-[N-(2-methylphenyl)sulfonyl]carboxamidomethoxy-4-methoxy]phenyl-1H-imidazol-5-yl]-2-[(2-methoxy-4,5-methylenedioxyphenyl)methyl]-2-propenoic acid;
E-3-[2-Butyl-1-[2-[N-(4-methylphenyl)sulfonyl]carboxamidomethoxy-4-methoxy]phenyl-1H-imidazol-5-yl]-2-[(2-methoxy-4,5-methylenedioxyphenyl)methyl]-2-propenoic acid;
E-3-[2-Butyl-1-[2-(N-dimethylaminosulfonyl)carboxamidomethoxy-4-methoxy]phenyl-1H-imidazol-5-yl]-2-[(2-methoxy-4,5-methylenedioxyphenyl)methyl]-2-propenoic acid;
E-3-[2-Butyl-1-[2-(N-methanesulfonyl)carboxamidomethoxy-4-methoxy]phenyl-1H-imidazol-5-yl]-2-[(2-methoxy-4,5-methylenedioxyphenyl)methyl]-2-propenoic acid;
E-3-[2-Butyl-1-[2-(N-t-butylsulfonyl)carboxamidomethoxy-4-methoxy]phenyl-1H-imidazol-5-yl]-2-[(2-methoxy-4,5-methylenedioxyphenyl)methyl]-2-propenoic acid;
E-3-[2-Butyl-1-[2-(N-i-propylsulfonyl)carboxamidomethoxy-4-methoxy]phenyl-1H-imidazol-5-yl]-2-[(2-methoxy-4,5-methylenedioxyphenyl)methyl]-2-propenoic acid;
E-3-[2-Butyl-1-[2-(2-(tetrazol-5-yl)benzyloxy-4-methoxy]phenyl-1H-imidazol-5-yl]-2-[(2-methoxy-4,5-methylenedioxyphenyl)methyl]-2-propenoic acid;
E-3-[2-Butyl-1-[2-(2-ethyl-3H-tetrazol-5-yl)benzyloxy-4-methoxy]phenyl-1H-imidazol-5-yl]-2-[(2-methoxy-4,5-methylenedioxyphenyl)methyl]-2-propenoic acid;
E-3-[2-Butyl-1-[2-[(4-carboxypyridin-3-yl)oxy]-4-methoxy]phenyl-1H-imidazol-5-yl]-2-[(3,4-methylenedioxyphenyl)methyl]-2-propenoic acid;
(E)-3-[2-Butyl-[1-(2-carboxymethoxy)-4-methoxy)phenyl]-1H-imidazol-5-yl]-2-[(2-methoxy-4,5-methylenedioxyphenyl)methyl]-2-propenoic acid; or
E-3-[2-Butyl-1-[2-(3-carboxy)propoxy-4-methoxy]phenyl-1H-imidazol-5-yl]-2-[(2-methoxy-4,5-methylenedioxyphenyl)methyl]-2-propenoic acid.

3. A compound of claim 1 which is (E)-3-[2-Butyl-1-[2-(2-carboxyphenyl)methoxy-4-methoxy]phenyl-1H-imidazol-5-yl]-2-[(2-methoxy-4,5-methylenedioxyphenyl)methyl]-2-propenoic acid.

4. A compound of claim 1 which is (E)-3-[2-Butyl-1-[2-[N-(phenylsulfonyl)]carboxamidomethoxy-4-methoxyphenyl]-1H-imidazol-5-yl]-2-[(2-methoxy-4,5-methylenedioxy)phenylmethyl]-2-propenoic acid dipotassium.

5. A pharmaceutical composition comprising an effective amount of a compound of claim 1 and a pharmaceutically acceptable carrier.

6. A method of treating hypertension, renal failure or cerebrovascular disease which comprises administering to a subject in need thereof, an effective amount of a compound of claim 1.

7. A method of treatment of congestive heart failure which comprises administering to a subject in need thereof, an effective amount of a compound of claim 1.

8. A method of treatment of migraine which comprises administering to a subject in need thereof, an effective amount of a compound of claim 1.

9. A method of treating restenosis which comprises administering to a subject in need thereof, an effective amount of a compound of claim 1.

* * * * *